United States Patent [19]

Verro

[11] 4,385,397

[45] May 24, 1983

[54] PARALLAX CORRECTED EXTERNAL ALIGNMENT LIGHTS

[75] Inventor: Piero Verro, Madison, Wis.

[73] Assignee: General Electric Company, Schenectady, N.Y.

[21] Appl. No.: 314,170

[22] Filed: Oct. 23, 1981

[51] Int. Cl.³ .................................................. A61B 6/00
[52] U.S. Cl. ...................................... 378/020; 378/206
[58] Field of Search ............................ 378/17, 20, 206

[56] References Cited

U.S. PATENT DOCUMENTS 4,167,675 9/1979 Stödberg ............................. 378/206
4,337,502 6/1982 Lescrenier .............................. 37/20

Primary Examiner—Eugene La Roche
Assistant Examiner—T. N. Grigsby
Attorney, Agent, or Firm—Wheeler, House, Fuller & Hohenfeldt

[57] ABSTRACT

External alignment lights mounted on the gantry of a tomography system to project on a staged patient a pattern showing the anatomy to be scanned by the system when the patient is translated form the staged position to the scanning position within the cylindrical opening of the gantry. Parallax correction means senses the angulation of the gantry with respect to the axis of translation of the patient table and modifies the translation distance of the table used to bring the patient into the scanning position.

9 Claims, 3 Drawing Figures

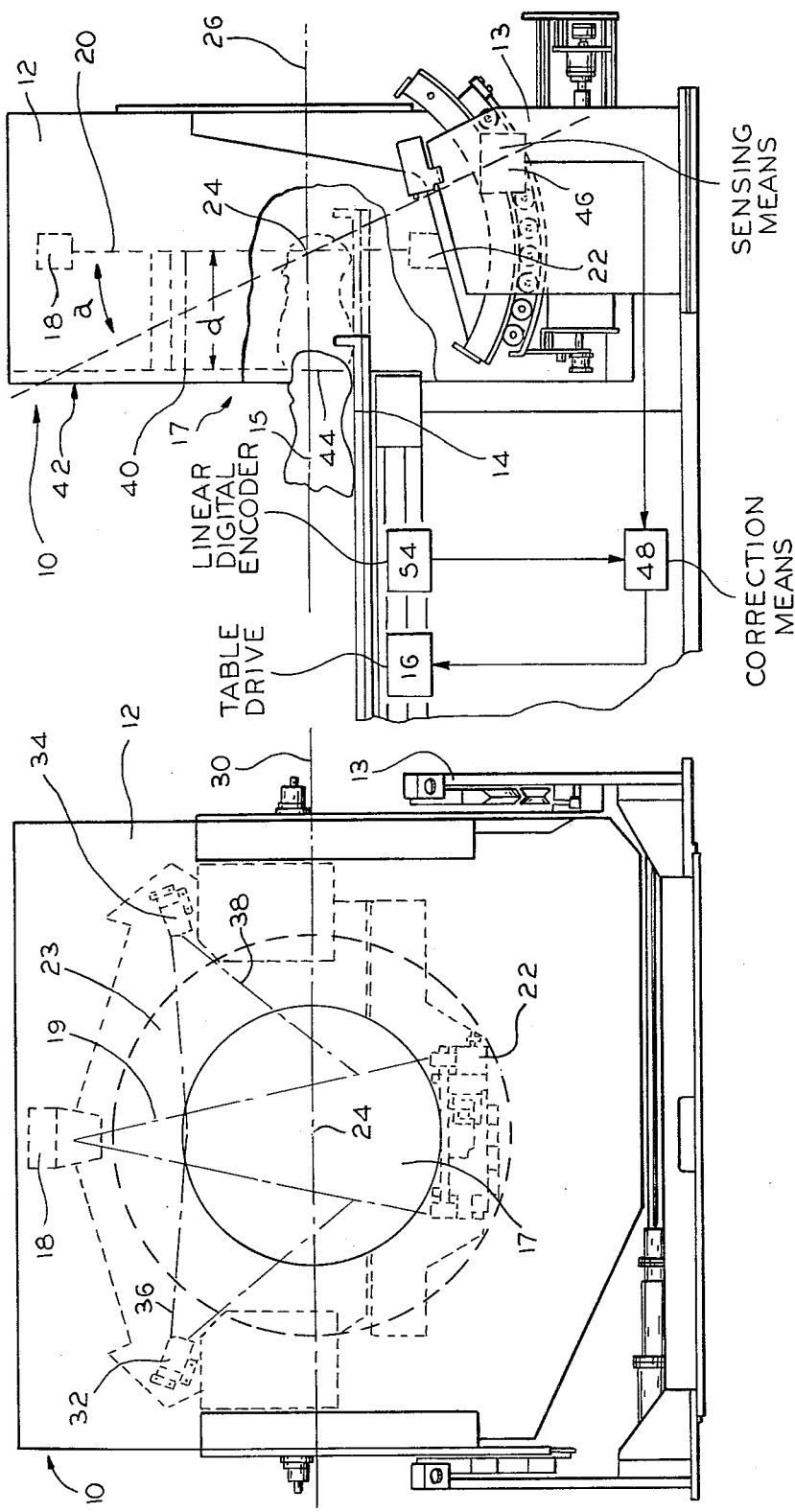

PARALLAX CORRECTED EXTERNAL ALIGNMENT LIGHTS

BACKGROUND OF THE INVENTION

This invention relates to the external alignment lights of a system for performing tomography. External alignment lights indicate the proper staged position of a patient prior to translating the patient to a scanning position for performing tomography.

Tomography is a technique for constructing a cross-sectional image of a patient. The anatomy to be studied is placed between a source of a fan shaped beam of penetrating radiation (typically X-rays) and a detector for such radiation. The source and detector are synchronously orbited about the patient, keeping the anatomy of interest in the plane of the radiation. Using the analog signals from the detector, the attenuation of the radiation by each point in the section of the patient being scanned can be determined and displayed as a cross-sectional image of the scanned area.

In a typical system for performing tomography, the radiation source and detector are mounted in a gantry for rotation about a generally cylindrical opening. The patient is positioned on a generally horizontal patient support or table. The table is translatable longitudinally into the cylindrical opening to move the patient from a staged position near or outside the opening to a scanning position within the opening. Either the gantry, the table, or both can be tilted to provide oblique scans through the patient.

It is known that to successfully scan the anatomy of interest the patient must be precisely positioned in relation to the scan plane.

One means for ensuring proper alignment of the anatomy of interest has been to project one or more beams of light on the patient to illuminate the anatomy which is then in the scan plane. Such lights, commonly called internal alignment lights, require the patient to be in the scanning position to check alignment. But the scan plane is deep within the gantry, making the position of the patient difficult to observe and adjust using internal alignment lights alone.

Another prior alignment system is shown in U.S. Pat. No. 4,117,337, issued to Staats on Sept. 26, 1978. This patent is hereby incorporated by reference. In this patent, external alignment lights project a pattern on the staged patient illuminating the section of the patient which will be in the scan plane when the patient is translated into the gantry. The longitudinal distance between the section of the staged patient defined by the external alignment lights and the scanning plane is equal to the programmed translation of the patient into the gantry. In the patented system, when the gantry or the patient table is rotated about a lateral tilt axis to provide oblique scans, the side alignment lights must be manually or mechanically tilted if they are to properly identify the scan plane. The ceiling mounted alignment light must be shut off altogether when the gantry or patient table is angulated, since the pattern it projects on the patient does not coincide with the portion of the staged patient to be scanned.

Another prior art alignment system uses an external alignment light mounted to the gantry to project a beam of light in a plane parallel to the scan plane. The pattern cast on the patient by such an external alignment light is subject to parallax when the gantry or the patient table is angulated. The prior art does not show how to compensate for this parallax error.

SUMMARY OF THE INVENTION

The present invention is an improved tomography system external alignment indicating means illuminating the portion of a staged patient which will be in the scan plane when the patient is translated into the gantry. At least one external alignment light source is mounted on the gantry for projecting a beam of light on the patient. The parallax error which results from angulation of the gantry or patient table is detected by a sensor which measures the degree of angulation between the patient table and gantry. Correction means are provided to modify the translation distance of the patient table to compensate for the parallax caused by gantry angulation. The result is an external patient alignment indication which precisely defines the resulting scan plane for all values of gantry angulations.

In the preferred embodiment of the invention two external alignment light sources are mounted on the gantry above and laterally to each side of the patient table. The light sources project coplanar fan shaped beams of laser light, illuminating a transverse line segment on the top and sides of the staged patient defining the proposed scan plane. The line segment can extend about 200° around the perimeter of the patient.

BRIEF DESCRIPTION OF DRAWINGS

FIG. 1 is a front elevational view of the gantry of a tomography system, showing the external alignment lights of the present invention.

FIG. 2 is a fragmentary side elevational view of the tomography system of FIG. 1, showing the patient in a staged position in full lines and in a scanning position in phantom.

DESCRIPTION OF A PREFERRED EMBODIMENT

Figure 3:
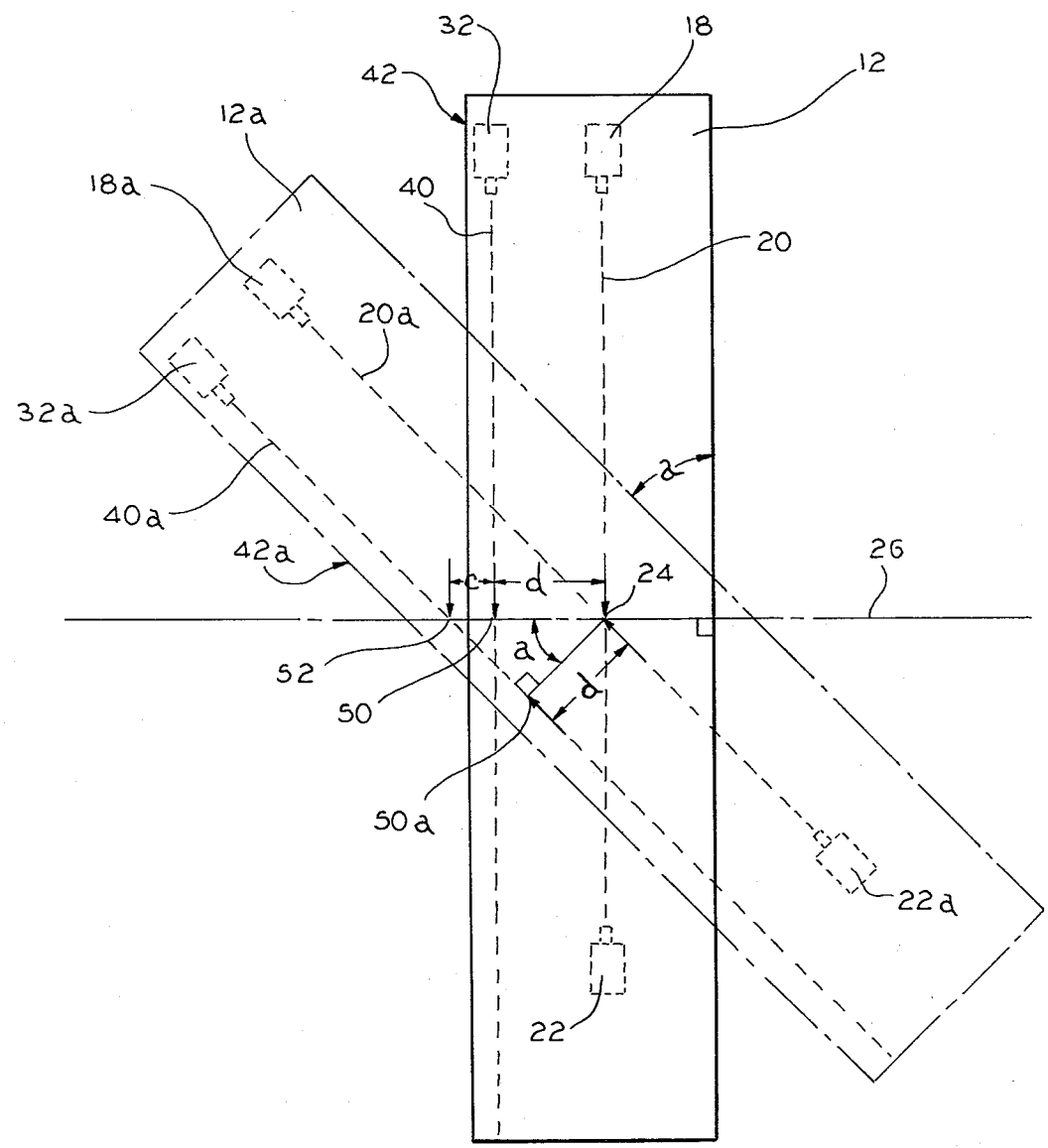
FIG. 3 is a schematic side elevational view of the gantry, demonstrating the existence of parallax and showing how to calculate the needed correction to the scanning position of the patient to account for parallax.

Although the disclosure hereof is detailed and exact to enable those skilled in the art to practice the invention, the physical embodiments herein disclosed merely exemplify the invention, which may be embodied in other specific structure. While the best known embodiment has been described, the details may be changed without departing from the invention, which is defined by the claims.

A detailed perspective view of the general layout of a tomography system is presented in FIG. 1 of the cited patent previously incorporated by reference.

Referring now to FIGS. 1 and 2, the tomography apparatus generally indicated at 10 comprises a gantry 12 and a patient table 14 to support patient 15. Table 14 has a drive 16 for translating the patient from a staged position (shown in full lines) to a scanning position (shown in phantom) well within the generally cylindrical opening 17 of the gantry. The gantry supports a source 18 of a fan shaped collimated beam 19 of penetrating radiation, typically X-radiation, which passes in plane 20 through patient 15 and is intercepted by a multiple cell detector 22. The detector cells detect the attenuation of each ray composing beam 19. Source 18 and detector 22 are mounted to a turret 23 for being synchronously orbited in the scan plane about an isocenter 24 defined by the point of intersection of scan plane 20 and the axis 26 of translation of the patient.

Gantry 12 is mounted to a base 13 for being tilted about a tilting axis 30 which passes through isocenter 24 for angulating gantry 12 with respect to axis 26. Of course, the same result could be obtained by tilting patient table 14. Angulation of the gantry or the patient table tilts scan plane 20 out of perpendicularity with axis 26, the degree of angulation being defined by angle (a) shown in FIG. 2.

The external alignment lights 32 and 34 are sources of collimated light, preferably laser beams, reflected from cylindrical mirrored surfaces to form fan shaped coplanar beams 36 and 38. Beams 36 and 38 are disposed in a plane 40 located just within the front 42 of gantry 12. The alignment lights project a pattern 44 which extends around at least a portion of the perimeter of the patient, preferably along about 200° of the perimeter. In this embodiment plane 40 is parallel to scan plane 20 and separated from the scan plane by a distance (d) which is equal to the distance table 14 translates into the gantry when scan plane 20 is perpendicular to the axis 26 of translation of the patient.

Alignment lights 32 and 34, although positioned slightly within the cylindrical opening 17, are defined herein as external alignment lights because they are external to the scan plane 20 and project a pattern on the patient which is easily visible from outside the gantry.

Alignment lights 32 and 34 are mounted to turret 23 for being orbited about isocenter 24 during scanning. But the invention would function equally well if the alignment lights were mounted to a nonrotating part of the gantry.

The other main parts of the present invention are sensing means schematically shown as 46 to detect the angulation of gantry 12 with respect to the translation axis 26 of patient table 14, and correction means schematically shown as 48 to modify the scanning position of the patient table to account for the parallax caused by gantry angulation.

FIG. 3 is a geometric construction showing how parallax arises from angulation of the gantry so that the lights 32 and 34 and the beams 36 and 38 are displaced from perpendicularity with axis 26. The line segment having endpoints 24 and 50 defines the distance (d) between scan plane 20 and the plane 40 of beam 38, equal to the required translation of the patient table to advance the patient from the plane of beam 38 to the scanning plane 20 when the gantry is vertical. When gantry 12 is angulated by an angle (a), the plane 40 defined by light 32 is displaced to the position indicated as 40a, striking axis 26 at point 52 instead of at point 50. The displacement of the intersection of plane 40 and axis 26 from point 50 to point 52 is the result of parallax. Point 52 is farther from the scanning plane than point 50 by the distance (c). In this instance the anatomy of interest must be translated laterally a distance of (c+d), or from point 52 to point 24, to reach the scanning position indicated on the staged patient by light 32a.

FIG. 3 also illustrates how to calculate the required correction to patient translation to account for parallax. A right triangle has one leg of length (d), a hypotenuse of length (c+d), and an included angle (a) equal to the degree of angulation of the gantry. The ratio of (c+d) to (d) is found to be the secant of angle (a). Therefore, the required translation (c+d) of the patient table along line 26 to account for parallax is given by the formula:

$$c+d=d \sec a$$

As an example of this calculation, if the required translation (d) between the staged and scanning positions is 50 centimeters when the gantry is vertical, the required translation (c+d) of the table when angle (a) is 20° is:

$c+d=d \sec a$ $d=50$ centimeters $a=20°$ $\sec a=1.06$ $c+d=(50 \text{ centimeters})(1.06)$ $c+d=53$ centimeters Thus, the patient table must be translated 53 centimeters when the gantry is angulated 20° in the illustrated embodiment of the invention. The foregoing formula will apply whether the gantry is angulated clockwise or counterclockwise, and whether the gantry, the table, or both are angulated. Of course, the required calculation would be different in other embodiments, such as one in which the scan plane was not parallel to the fan shaped beams of the alignment lights.

The scanning position of patient table 14 can be changed to account for parallax as follows if advancement of table 14 to the scanning position is regulated by a microprocessor. Sensing means 46 is an angular digital encoder which maintains a digital value corresponding to the angular position of gantry 12 with respect to its base. (In this embodiment the patient table is not angulated.) Correction means 48 is a microprocessor which has stored in its memory a value for the required table translation from the staged position to the scanning position when the gantry is vertical. Table 14 has a linear digital encoder 54 which maintains a digital value corresponding to the position of the table with respect to its base. When the patient table is to be advanced, the microprocessor reads linear encoder 54 to establish a landmark position for the patient table, it reads angular encoder 46 to determine gantry angulation, it performs the calculation shown previously for parallax correction, and it updates the value for patient table translation stored in its memory to correct the parallax error. The microprocessor then instructs the table drive 55 to advance the table until the value read in the linear encoder is equal to the sum of the landmark position and the updated value for table translation. The table is then in the corrected scanning position.

I claim:

1. In a tomography system including a gantry having a generally cylindrical opening to receive a patient, a patient table longitudinally translatable to move the patient from a staged position to a scanning position within the gantry opening, means to tilt at least one of said patient table and said gantry about a lateral tilting axis to provide oblique scans, and external alignment light means mounted on said gantry for indicating on the staged patient the portion of the patient to be scanned, parallax correction means comprising:

sensing means to detect the angulation of said gantry with respect to said patient table; and correction means to modify the translation distance of said patient table when advancing to scan plane to compensate for the parallax caused by gantry angulation.

2. The tomography system of claim 1, wherein said light means is a laser.

3. The tomography system of claim 1, wherein said gantry is tiltable about said tilting axis.

4. The tomography system of claim 3, wherein said light means is mounted on said gantry substantially above said tilting axis.

5. The tomography system of claim 3, wherein said tilting axis passes through the isocenter of said gantry.

6. The tomography system of claim 1, wherein said light means comprises first and second sources of a fan shaped beam of light mounted on said gantry, said first and second light sources being respectively fixed to the right and to the left of the axis of translation of said patient table.

7. The tomography system of claim 6, wherein said first and second light sources project a pattern along about 200 degrees of the perimeter of said patient.

8. The tomography system of claim 1, wherein said sensing means comprises an angular digital encoder which maintains a digital value corresponding to the angular position of the gantry with respect to its base.

9. The tomography system of claim 8, wherein patient table translation is governed by a microprocessor, patient table position is recorded by a linear digital encoder, and said parallax correction means comprises:

memory means to store a value for translation distance of said table from said staged position to said scanning position when said gantry is perpendicular to said table;

means to read said linear encoder to establish a landmark value for the staged position of said table;

means to read said angular digital encoder to establish a gantry angle;

means to multiply said stored value for translation by the secant of said gantry angle, whereby to derive an updated value for patient table translation distance;

means to add said updated value for translation distance to said landmark value to derive a value for the corrected scanning position of said table; and means to drive said table into said gantry until said linear digital encoder indicates a value for table position equal to said value for corrected scanning position.

* * * * *